(12) United States Patent
Forman et al.

(10) Patent No.: US 7,815,561 B2
(45) Date of Patent: Oct. 19, 2010

(54) BRACHYTHERAPY APPLICATOR

(75) Inventors: Michael R. Forman, Los Gatos, CA (US); Darius Francescatti, Barrington, IL (US); Ni Ding, San Jose, CA (US)

(73) Assignee: Xoft, Inc., Sunnyvale, CA (US)

( * ) Notice: Subject to any disclaimer, the term of this patent is extended or adjusted under 35 U.S.C. 154(b) by 1428 days.

(21) Appl. No.: 10/742,445

(22) Filed: Dec. 19, 2003

(65) Prior Publication Data

US 2005/0070753 A1    Mar. 31, 2005

Related U.S. Application Data

(60) Provisional application No. 60/505,440, filed on Sep. 25, 2003.

(51) Int. Cl.
*A61N 5/00* (2006.01)
(52) U.S. Cl. ......................................... 600/3
(58) Field of Classification Search ................. 600/1–9, 600/431; 623/8, 23.75
See application file for complete search history.

(56) References Cited

U.S. PATENT DOCUMENTS

| 6,214,045 B1 | 4/2001 | Corbitt, Jr. et al. |
| 6,248,057 B1 | 6/2001 | Mavity et al. |
| 6,270,464 B1 | 8/2001 | Fulton, III et al. |
| 6,413,204 B1 | 7/2002 | Winkler et al. |
| 6,749,555 B1 * | 6/2004 | Winkler et al. ................. 600/3 |
| 2001/0041936 A1 | 11/2001 | Corbitt, Jr. et al. |
| 2002/0029083 A1 | 3/2002 | Zucherman et al. |
| 2002/0035168 A1 | 3/2002 | Loomis et al. |
| 2002/0165337 A1 | 11/2002 | Wallace |
| 2003/0083389 A1 | 5/2003 | Kao |
| 2003/0224465 A1 * | 12/2003 | Nevalainen et al. ......... 435/7.23 |
| 2004/0116767 A1 * | 6/2004 | Lebovic et al. ................. 600/7 |

OTHER PUBLICATIONS

Formation of highly porous biodegradable scaffolds for tissue engineering, Antonios G. Mikos, *Electronic Journal of Biotechnology*, ISSN: 0717-3458, vol. 3, No. 2, Aug. 15, 2000.
Fabrication of porous gelatin scaffolds for tissue engineering, Hye-Won Kang et al., *Biomaterials 20*, 1999, 1339-1344.
Limited Field Radiation Therapy in the Management of Early-Stage of Breast Cancer, *The Journal of the National Cancer Institute*; vol. 95, 16, Aug. 20, 2003.

* cited by examiner

*Primary Examiner*—Charles A Marmor, II
*Assistant Examiner*—Christine D Hopkins
(74) *Attorney, Agent, or Firm*—Thomas M. Freiburger

(57) ABSTRACT

A breast brachytherapy applicator providing a stable semi permanent/permanent in dwelling platform that is configured to replicate anatomically the excised cancer bed and allows for a more precise anatomically correct delivery of limited field radiation treatment. This device may be used to reconstitute a resected tissue space to its pre-operative size and shape to 1) facilitate the accurate and precise delivery of adjunctive breast brachytherapy following breast cancer surgery and 2) prevent/decrease post-operative deformity as a result of surgical resection, whether for benign or malignant disease, and in particular after radiation treatment of malignant disease in the post lumpectomy patient.

8 Claims, 9 Drawing Sheets

BRACHYTHERAPY APPLICATOR

The present application claims priority under 35 U.S.C. §119 to U.S. Provisional Patent Application Ser. No. 60/505,440, filed Sep. 25, 2003, the disclosure of which is incorporated in its entirety herein by reference.

BACKGROUND OF THE INVENTION

1. Field of the Invention

The present invention relates generally to the field of surgery and post-surgical radiation for the treatment of cancer. Specifically, the present invention relates to the field of breast brachytherapy for the adjunctive treatment of breast cancer.

2. Description of the Related Art

Breast cancer patients receiving a partial mastectomy (lumpectomy) with or without axillary sampling of lymph nodes are given radiation therapy to the remaining breast tissue of the cancerous breast as an integral and essential element for the ablation of any remaining residual undiscovered microscopic foci of cancer.

Today, the delivery of adjuvant radiation to the surgically treated breast is done utilizing either whole breast radiation or brachytherapy (limited field) radiation.

Whole Breast Radiation:

Whole breast radiation has been the standard method of adjuvant breast radiotherapy employed until relatively recently. It has been shown to be extremely effective in preventing breast cancer recurrence in women treated with conservative breast surgery ("Limited Field Radiation Therapy in the early Stage of Breast Cancer". The Journal of the National Cancer Institute: Vol. 95, 16). However, whole breast adjuvant radiation is associated with patient morbidity that is seen in both the acute (at or near the time of radiation treatment) and chronic time periods (months to years after treatment has been given). Any tissue within the field of treatment can be adversely affected; this includes the skin, muscles, bone, heart, and lung; as an example, acute morbidity can include skin burn and a chronic sequela is sarcomatous cancer arising in previous irradiated tissue years after treatment. Now, questions have also arisen regarding the need and/or efficacy of treating all breast tissue in the involved breast. Comparison of patients receiving whole breast radiation versus limited field radiation to the lumpectomy site showed the following results over a five year period: there is no difference in the median time to recurrence or rate of local recurrence regardless of mode of radiation therapy i.e. whole breast versus limited field, and that there is no difference between groups in rate of overall survival, disease free survival or in the rate of distant spread of the cancer (beyond the breast). An additional shortcoming in the delivery of standard whole breast radiation to the surgically treated breast requires the delivery of this treatment course over an extended period of time (5-6 weeks on average). Because of this, patient compliance consisting of a daily five-day course of radiation treatment (weekends and holidays excepted) for an extended period of 5-6 weeks is the norm. This regimen is burdensome to many rural and elderly patients who cannot economically or practically commute to a treatment center or who, because of age or disability, cannot meet these requirements for treatment. The result of this inability to undergo whole breast radiation treatment results in the total surgical excision of the breast, a mastectomy.

Brachytherapy:

Recently, limited field radiation therapy, known as brachytherapy, has been shown to be an effective method of delivering radiation therapy to patients who have undergone breast-conserving surgery ("Limited Field Radiation Therapy in the early Stage of Breast Cancer". The Journal of the National Cancer Institute: Vol. 95, 16). Because of the present day inability to definitively surgically eradicate all cancer bearing tissue at the site of operation in the breast, radiation treatment is delivered to the site of surgical excision to incorporate a 2-3 cm rim of normal appearing tissue on all sides of the surgical cavity. All remaining breast tissue is not irradiated. Treatment performed utilizing brachytherapy as an adjunct to the surgical excision of a breast cancer is done in a markedly shortened treatment interval (five day limited field radiation schedule versus five weeks whole breast) and, because of this, will provide those patients unable to undergo a four to six week treatment regimen of whole breast radiation an alternative treatment choice other than total mastectomy. And, because of the methodology used, only the breast tissue at greatest risk of recurrence is treated thereby reducing the morbidity seen in the whole breast radiation treatment.

Even the application of brachytherapy to the cancerous bed of resected lumpectomy specimens has undergone a genesis since its inception. It is delivered, at present, using one of two techniques. The first technique employs the percutaneous placement of multiple treatment rods through the breast in a configuration that allows for the delivery of a specific radiation dose to a specific area of residual targeted breast tissue in the post lumpectomy patient. Multiple skin entrance and exit sites are created with resultant scarring and, because of the need for multiple delivery devices, patient acceptance is limited. An alternative method for Brachytherapy treatment utilizes a catheter device that is placed into the surgically excised bed either operatively or post-operatively allowing for the delivery of a five-day course of radiation treatment. Because the Proxima brachy catheter device (Proxmia Therapeutics Inc., Alpharetta, Ga.) relies on a distensible balloon for placement within the surgical cavity prior to delivery of treatment, a spherical surgical cavity is required. However, the surgical excision of a breast cancer is not performed in a standardized manner because breast cancers by their very nature do not grow and proliferate exactly alike. Examples of breast cancer geometries include spherical, stellate (radiating arms of breast cancer proliferation of unequal length extending unequally in various directions), and linearly directed (breast cancers growing along the axis of a specific duct). These examples hint at the variability of size and shape of cancers encountered routinely during surgical excision. And so the cancer is excised in a blind fashion by excising tissue by feel; this results in a jagged cavity of uneven dimensions which must then be made circular by approximating the cavity circumference around the spherical applicator balloon. The spherical device can not precisely occupy the surgically excised tumor bed and requires further surgical manipulation and fixation of tissues in non-anatomical positions to achieve this goal. In other words, the surgeon in utilizing this mode of therapy must reconfigure the surgical cavity to "fit the device".

The creation of any surgical cavity, by necessity, will form a deformity in the tissue bed from which it is excised. The result is an anatomic deformity that may or may not be apparent on the skin surface. The deformity created in the breast by excision of tissue, whether for benign or malignant disease, is a routine consequence of breast surgery. This defect, however, is markedly compounded by the addition of radiation therapy, whether by whole breast or limited field application. And it is further compounded by the surgical reapproximation and reshaping required for the proper seating of brachytherapy delivery devices that utilize a fixed shape. (The breast, as a skin appendage, is important functionally, aesthetically and is of paramount importance in a personal sense to a healthy body image.)

Radiation Dose Delivery:

Radiation dose delivery to targeted tissue is determined by the physics inherent in the production of radioactive or highly energetic photon energy. Delivery of a specific dose to a targeted area is also dependent on the ability to fix the delivery device (a stable platform) so that each successive treatment adds a further increment of radiation energy only to the targeted tissue. Any change in delivery device position can result in either over or under treatment to the area of targeted tissue or the adjacent tissue, i.e., skin, muscle, or non-targeted breast; this will cause morbidity to surrounding structures. Furthermore, the necessity of surgically shaping breast tissue around a delivery device can result in an area of tissue requiring treatment of being excluded because of the anatomic disruption caused by this additional surgical maneuver.

Notwithstanding the foregoing, there remains a need for improved methods and devices for use in targeted brachytherapy of soft tissue.

SUMMARY OF THE INVENTION

The methods and devices in accordance with the present invention provide a stable semi permanent or permanent in dwelling platform that is configured to replicate anatomically the excised cancer bed and allow for a more precise anatomically correct delivery of limited field radiation treatment. The device may be used to reconstitute a resected tissue space to its pre-operative size and shape to 1) facilitate the accurate and precise delivery of adjunctive breast brachytherapy following breast cancer surgery and 2) Prevent/decrease post-operative deformity as a result of surgical resection, whether for benign or malignant disease, and in particular after radiation treatment of malignant disease in the post lumpectomy patient.

Although the present invention will be described primarily in the context of treatment and surgery of the breast, it can be used in any area of the body requiring sculpting of tissue either as a result of a deformity resulting from excised tissue or as a de novo tissue replacement for reconstructive or constructive surgery.

There is provided in accordance with one aspect of the present invention, a method of treating a patient. The method comprises the steps of identifying a patient having a cavity formed by the removal of tissue. The cavity is filled with a volume of material, which approximates the volume of removed tissue. A guide tube may be positioned through the material, and a radiation source is positioned within the guide tube.

The identifying a patient step may comprise identifying a breast lumpectomy patient. The filling the cavity step may comprise introducing a hydrogel into the cavity. In general, a bioresorbable media may be introduced into the cavity. In one implementation, a porous, bioresorbable, biocompatible tissue support scaffold is introduced into the cavity.

The positioning a guide tube step may comprise advancing a hollow trocar through the material, advancing the guide tube through the trocar, and removing the trocar to leave the guide tube in place through the material.

In accordance with another aspect of the present invention, there is provided a method of performing brachytherapy following breast cancer surgery. The method comprises the steps of performing a surgical resection of a breast, leaving a surgically excised cavity surrounded by a margin of remaining tissue. A stabilizing media is introduced into the cavity, operatively or post operatively to anatomically fix the position of the margin. At least one radiation dose is delivered from within the cavity into and optionally through the margin of tissue.

The introducing a stabilizing media step may comprise introducing a stabilizing media into the cavity to retain the pre-excisional anatomical position of the margin. The method may additionally comprise the step of positioning a guide through the media, for guiding a source for the radiation dose. Preferably, the guide is positioned along a predetermined axis of optimal radiation therapy.

In accordance with a further aspect of the present invention, there is provided a method of positioning a brachytherapy guide through a surgically excised cavity. The method comprises the steps of creating a cavity by excising a volume of tissue, the cavity defined within a margin of remaining tissue. A bulking media is introduced into the cavity, to stabilize the original anatomical position of the margin. The location of the margin is imaged, and at least one axis of desired radiation therapy is determined taking into account the resultant postsurgical position of the margins. A brachytherapy guide is introduced along the axis to enable controlled delivery of radiation.

The introducing a brachytherapy guide step may comprise introducing a trocar along the axis, and advancing the guide along the path of the trocar. The method may additionally comprise the step of removing the trocar, leaving the guide in place along the axis.

In accordance with a further aspect of the present invention, there is provided a method of reducing post-operative deformity as a result of surgical resection in soft tissue. The method comprises the step of removing soft tissue from a treatment site, leaving a cavity surrounded by a surface on the adjacent remaining tissue. A bulking media is introduced into the cavity, to fill the cavity and maintain the surface approximately in its pre-excisional anatomical position before the removing step. The bulking media is permitted to gradually be replaced by normal biological repair processes.

The removing soft tissue step may comprise removing benign tissue, or removing malignant tissue. The method may additionally comprise the step of delivering at least one dose of radiation to the surface from within the cavity. The dose of radiation may be delivered from a guide tube extending through the bulking media.

At least two doses of radiation may be delivered, spaced apart in time. In accordance with one dosing regime, two fractions per day are delivered for a period of 5 days, with each fraction approximately 3.2 Gy.

In accordance with another aspect of the present invention, there is provided a method of treating a patient. The method comprises the steps of removing a volume of tissue from a patient, leaving a cavity surrounded by a margin of tissue. The margin is maintained in approximately its original anatomical position as before the removing step. The margin is thereafter exposed to radiation either with brachytherapy or conformal radiation. The maintaining step may be accomplished by filling the cavity with a support scaffold such as a bulking media.

In accordance with another aspect of the present invention, there is provided a brachytherapy delivery system. The system comprises an elongate tubular trocar, having a proximal end and a distal end. A brachytherapy guide tube is axially advanceable into the proximal end of the trocar. A connector, for connecting the trocar to the guide tube while permitting axial movement of the guide tube with respect to the trocar is also provided.

The connector may be flexible. In one implementation of the invention, the connector comprises a suture. The proximal end of the guide tube may additionally be provided with a closeable port, such as a pierceable septum.

In accordance with a further aspect of the present invention, there is provided a brachytherapy delivery system. The system comprises an elongate brachytherapy guide tube, having a proximal end and a distal end. A pierceable septum is provided on the proximal end. A tubular trocar is removably attached to the distal end.

In accordance with a further aspect of the present invention, there is provided a brachytherapy delivery system. The system comprises an elongate brachytherapy guide, having a proximal end and a distal end. A first tissue attachment structure is provided on the proximal end for attachment to a first tissue surface, and a second tissue attachment structure is provided on the distal end, for attachment to a second tissue structure.

The first tissue attachment structure may comprise an elastomeric septum. The second tissue attachment structure may comprise a suture.

Further features and advantages of the present invention will become apparent to those of ordinary skill in the art in view of the detailed description of preferred embodiments which follows, when considered together with the attached drawings and claims.

DETAILED DESCRIPTION OF THE PREFERRED EMBODIMENT

Figure 1:
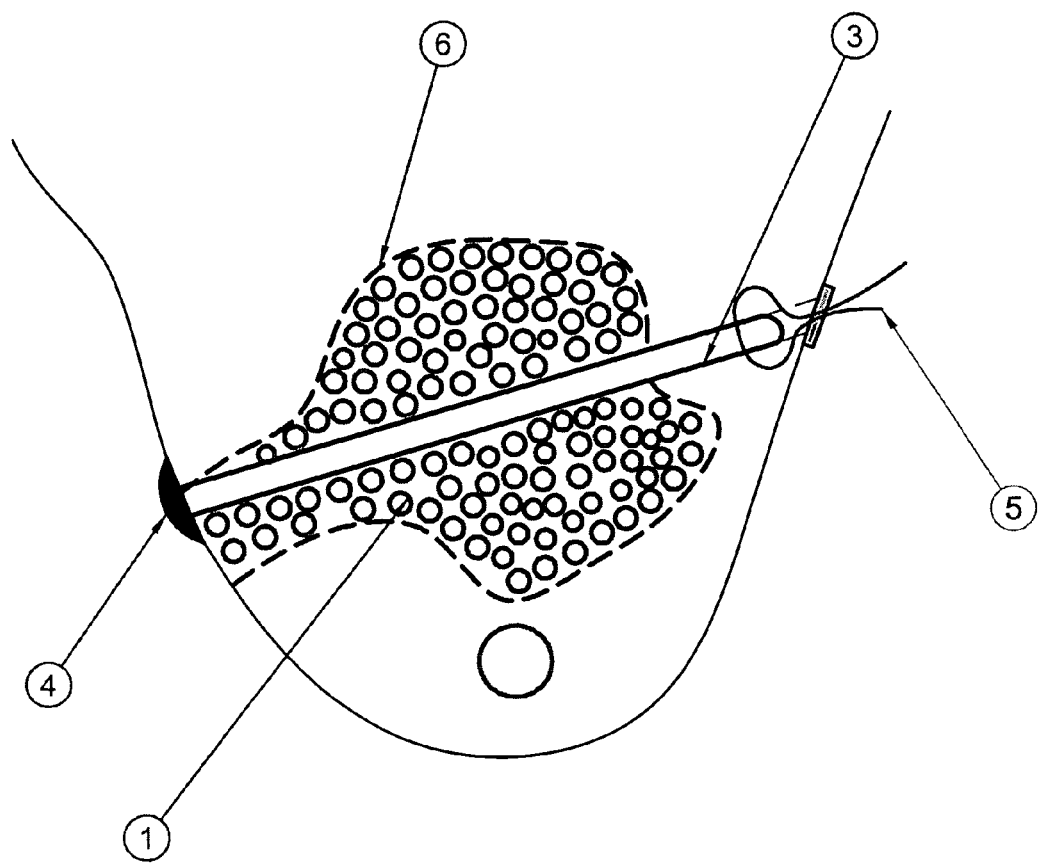
FIG. 1 shows the breast brachytherapy applicator positioned in the resected cavity.

Malignant tumors when surgically resected leave excavated cavities of various dimensions and configurations in the operated breast. Because of present day inability to definitively surgically eradicate all cancer bearing tissue at the site of operation, radiation treatment is delivered to the site of surgical excision to incorporate a 2-3 cm rim of normal appearing tissue on all sides of the surgical cavity. However, the geometry of a lumpectomy cavity is predicated on the particular geometry of the resected breast cancer and, because of this, is usually irregular in geometric shape. Because of this, the delivery of radiation treatment to the surgical rim cannot be uniformly delivered utilizing present day brachytherapy delivery systems. As an example, the Proxima system requires shaping of the remaining unresected breast tissue around a form.

The present invention is designed to position and support the lining tissue from the surgically excised cavity to its natural contour by forming within the surgical cavity a permanent or degradable support. The present invention also enables calculation of actual excised tissue volume and acts as an anatomical surrogate for the excised cancerous tissue, allowing precise dosimetry calculations to be formulated along real anatomic boundaries unaffected by further surgical distortion. The present invention also provides a stable, reproducible, semi-permanent to permanent mold through which a brachytherapy delivery device can be positioned under precise CT or ultrasound guidance to insure the optimal delivery of the therapeutic radiation dose to targeted tissues. The present invention provides a stable scaffold maintaining the anatomically correct relationship of the remaining breast tissue vis-à-vis the excised tissue in order to precisely delivery conformal radiation or brachytherapy.

With the maturation of the porous, bioresorbable, biocompatible tissue support scaffold, interstitial spaces (pores) will be created between the latticework of the support scaffold. This provides for the accumulation and distribution of the normal post operative fluid effusion (seroma) throughout the newly excised surgical cavity. The effusion of this fluid will replace in a volumetric manner the gradual biologic degradation of the porous, bioresorbable, biocompatible tissue support scaffold, thereby strengthening the borders of the cavitary tissue mold. This will lessen or prevent the contour deformity of the breast commonly seen after either surgical or radiotherapeutic treatment. In addition to its ability to sequester and constructively utilize seroma fluid post treatment, any of a variety of biocompatible chemo-therapeutic, chemo-preventive agent, antibiotic or any substance found to enhance the delivery of radiotherapy to the surrounding breast tissue can be bound to the porous, bioresorbable, biocompatible tissue support scaffold, and thereby be incorporated into the organic/inorganic make up of the cavitary matrix.

A porous, bioresorbable, biocompatible tissue support scaffold may be delivered into the surgical cavity at the completion of the operation or, in another application, during the postoperative period in those patients determined to be candidates for Brachytherapy treatment. Terms and phrases such as porous bioresorbable biocompatible tissue support scaffold, bulking media, media, and the like may be used interchangeably throughout this specification. In general, the media or bulking media may be in any of a variety of liquid, semi-liquid or solid forms, which can be caused to conform to the irregular contours of a tissue cavity and act as a scaffold to approximate the volume and shape of the excised tissue.

If the porous, bioresorbable, biocompatible tissue support scaffold is injected at the time of surgery, the skin closure of the incision will be performed after placement of an injection port that utilizes the skin closure site or a newly formed para incisional site. The porous, bioresorbable, biocompatible tissue support scaffold will be then be injected either under direct vision or aided by real time operative ultrasound. In this fashion the volume of injected tissue support scaffold can be tactically and visibly monitored to insure that the surgical cavity is reconstructed in its entirety. A precise volume assessment of the surgical cavity can be inferred by noting the cc volume of bulking agent used. The volumetric distention of the surgical cavity can also be monitored utilizing intra operative sonography if so desired. The operative phase is completed by withdrawing the injection port in either instance and the application of postoperative dressings.

Certain bulking agents may undergo a volume change as they transform from a flowable, injectable form to a polymerized or otherwise hardened or gel form for providing a tissue scaffold as described herein. In this case, the volumetric assessment will involve a calculation which take into account the volume change upon transformation of the bulking media, as will be understood by those of skill in the art in view of the disclosure herein. Alternatively, for bulking agents which do not undergo a transformation in volume, the precise volume assessment may be accomplished by simply monitoring the volume of infused media.

The postoperative infusion of porous, bioresorbable, biocompatible tissue support scaffold for the reconstruction of the surgical bed is done in a similar fashion and facilitated by either placement of the injection port through the post operative incision or by the para incisional creation of a percutaneous tract through the pseudo capsule of the resected tissue. This postoperative placement of an injection port can be aided by real time sonography or other imaging modalities. Any residual seroma is evacuated prior to the injection of the hydrogel. Once again, the tissue support scaffold is injected under visual, tactile and real time sonographic scanning until the surgical cavity is filled.

The operative injection of porous, bioresorbable, biocompatible tissue support scaffold will additionally facilitate, if the need should arise, of any further surgery necessitated at the lumpectomy site for "an involved margin". This contingency can result from the finding of an involved cancerous margin i.e. a cancer containing border (outer rim) of the lumpectomy specimen, during pathologic assessment. This finding mandates reoperation and the reexcision of any portion of the involved lumpectomy circumference (rim). This re-excision will be facilitated by having a stable tissue mold in place that will provide the surgeon with directional tactile and visual cues during the re-excision process. After completion of the re-excision, tissue support scaffold is infused into the newly created surgical cavity as initially performed. This re-excision provides an easily imaged target for the percutaneous image directed excision of additional tissue.

Because of porous, bioresorbable, biocompatible tissue support scaffold preset fluid properties during the injection phase, the resultant hydrogel mold will fill the surgical cavity by utilizing the geometry of the lumpectomy site as its insitu mold. The result is a mold that replicates anatomically the configuration of the surgical cavity. No additional surgical manipulation or suturing of the lumpectomy site or surrounding tissue is required.

Radiation dosimetry planning utilizing advanced imaging devices can now be done with greater accuracy because the para lumpectomy breast tissue that may harbor residual microscopic foci of breast cancer remains in its normal anatomic relationship to the excised cancer. The ability to deliver an optimal radiation therapy conducive to treatment of a surrounding rim of breast tissue to the accepted parameters of treatment regardless of excisional geometry of the surgical site, is technically facilitated. The optimal treatment axis (or axes for complex shaped excisional cavities) can be determined and is consistently reproducible because of the stability of the tissue mold and its relationship to the surrounding breast tissue.

Once the axis of the optimal treatment is determined, the percutaneous insertion of the Brachytherapy delivery device can be done under advanced imaging methodology and then utilized throughout the course of treatment.

Axial stabilizing device(s) which include a canula, trocar and a cutaneous anchoring system is inserted utilizing local anesthesia at the skin sites. Once placed, it is anchored to the skin at entrance and exit sites to ensure stability and is easily removed at the completion of the treatment regimen. The positioning of the axial stability device is facilitated utilizing advanced imaging to assure the most precise placement along the predetermined axis of optimal radiation therapy conducive to treatment of a 2 cm rim of surrounding breast tissue regardless of excisional geometry. One or more axial stabilizing devices can be used, depending on the determination by a radiation physicist on the requirements for a uniform distribution of radiation within the target tissue.

The porous, bioresorbable, biocompatible tissue support scaffold utilized for cavitary molding will be in either a permanent or semi permanent (e.g., absorbable) form. In either form, it will provide additional benefits in addition to providing a stable and structurally supporting medium for placement of the percutaneous delivery device. By virtue of its volumetric presence in the surgical cavity, it will retard or prevent the development of contractual scar formation at the surgical site and resultant contour deformity. This will result in enhanced cosmetic outcomes after surgical or surgical/radiotherapeutic procedures for breast mastopathies.

At the completion of radiotherapy, the axial "positional" stabilizing device(s) is withdrawn by releasing the anchoring mechanism at both entrance sites and withdrawing the canula. Dressings are then placed and wound healing allowed to occur. The presence of a permanent marker (tissue mold) in the configuration of the initial lumpectomy cavity will facilitate better long-term analysis utilizing radiography, sonography, advanced imaging techniques including CT and MRI of the surrounding rim of treated tissue. In the event that a semi permanent mold has been used, the replacement of the hydrogel by seroma fluid will act in a similar fashion for the long term assessment of the treated cancerous site.

Figure 2:
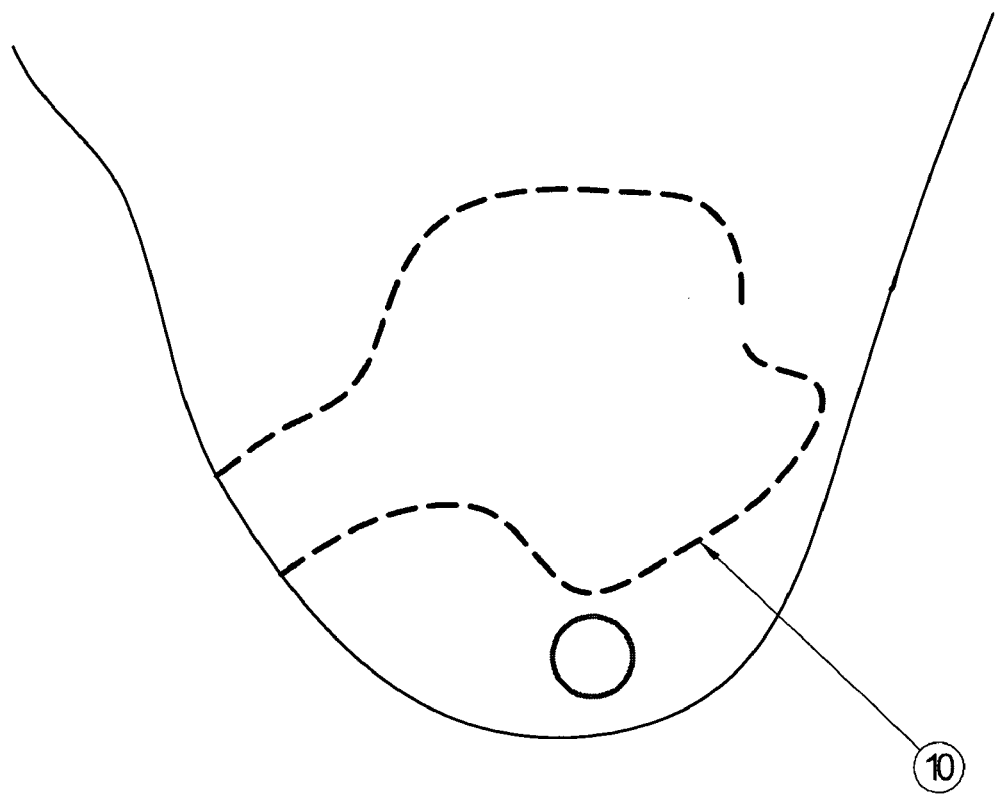
FIG. 2 illustrates the resected cavity.
Figure 3:
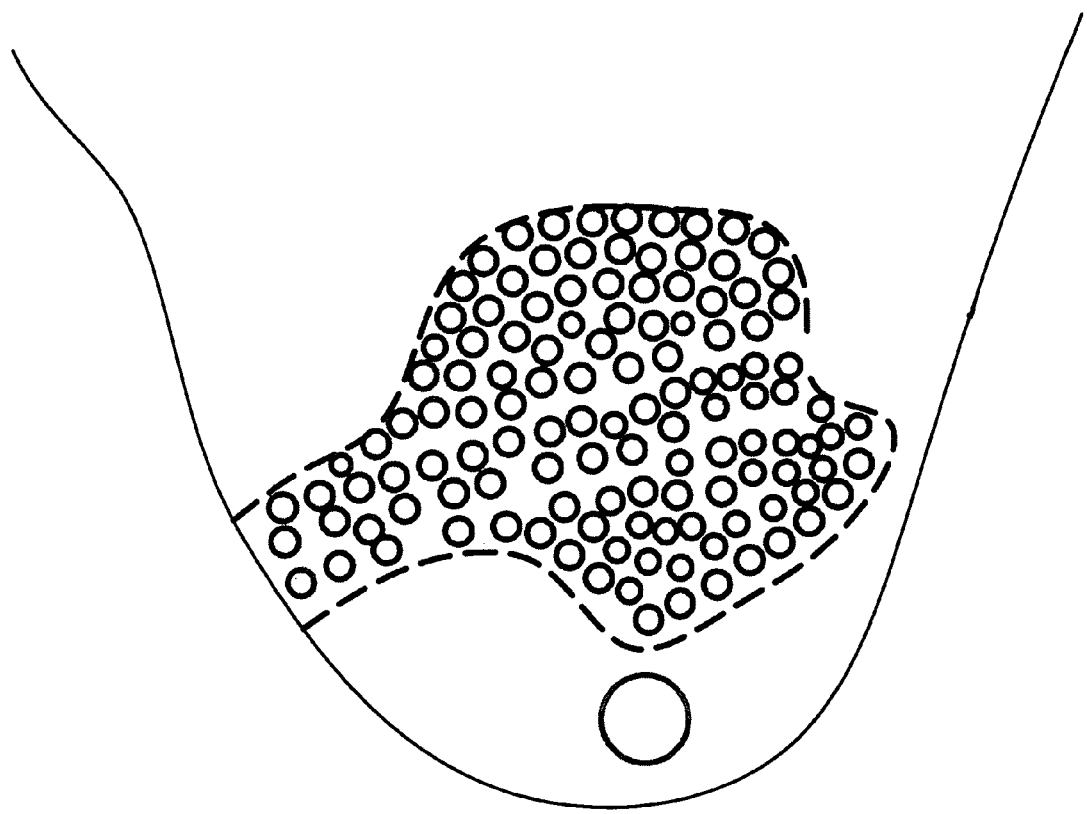
FIG. 3 illustrates the resected cavity filled with a bioresorbable, biocompatible, porous tissue support scaffold.

Referring to FIGS. 1 through 7, one embodiment of a brachytherapy applicator system in accordance with the present invention may include 5 main components: a biocompatible bulking media or tissue scaffold (1), a hollow trocar (2), a brachytherapy guide such as a tube (3), an elastomeric septum attached to the brachytherapy guide (4) and connectors such as sutures (5) connecting the trocar and guide tube. FIG. 2 shows the surgical cavity (10) after lumpectomy or wide surgical excision. The bulking media, such as a porous, bioresorbable, biocompatible tissue support scaffold (1) is shown filling the surgical cavity (6) in FIG. 3.

Figure 4:
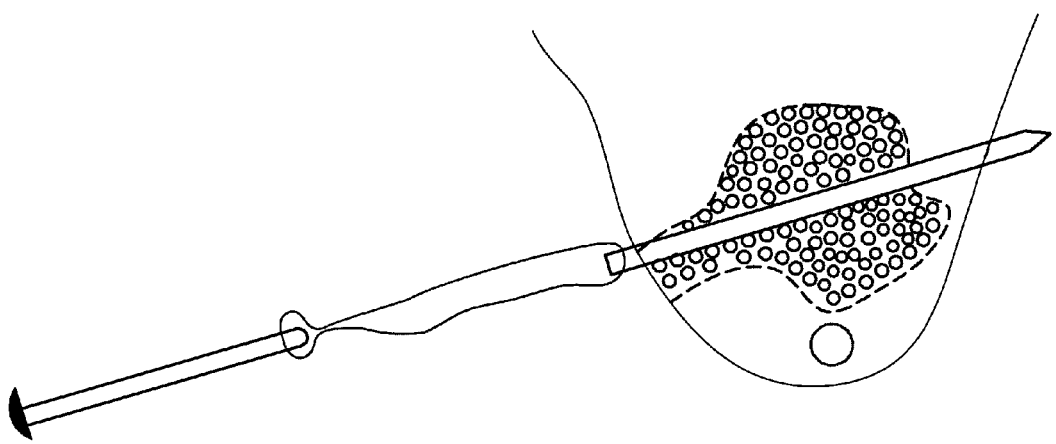
FIG. 4 illustrates the trocar positioned in the resected cavity and the brachytherapy guide tube attached to the trocar with sutures.

FIG. 4 illustrates a second step in the procedure. Hollow trocar (2) is inserted through the surgical cavity, along a predetermined axis such as the long axis of the cavity, which is centered in the irregular cavity. Hollow trocar (2) pierces the skin on the near side of the breast and on the far side of the breast. Hollow trocar (2) is of a generally tubular shape and can be made of a metal or a polymer. The trocar preferably has a closed distal end. It has sufficient rigidity to pierce the tissue and traverse the implant material without being deflected. In general, the hollow trocar (2) will have a diameter with the range of from about 3 mm to about 6 mm, and an axial length within range of from about 5 cm to about 12 cm. The hollow trocar (2) may have an outside diameter of preferably no more than about 6 mm, and an inside diameter sufficient to receive the brachytherapy guide tube (3), which will often have an outside diameter no more than about 5 mm. Hollow trocar (2) may be provided with a sharpened distal end to facilitate soft tissue penetration as is understood in the art. Any of a variety of other dimensions or configurations may also be used, depending upon the intended clinical performance.

Hollow trocar (2) is connected to brachytherapy guide tube (3) by a flexible and/or extendable connector such as sutures (5). Sutures (5) may be attached to the proximal end of the hollow trocar (2) and the distal end of brachytherapy guide tube (3). The brachytherapy guide tube is made of any of a variety of materials known in the art that are generally transparent to x-rays, beta rays and/or gamma rays. Many polymers are suitable to pass these highly energetic photons, so that most of the photons are absorbed by the tissue, rather than the guide tube.

Figure 5:
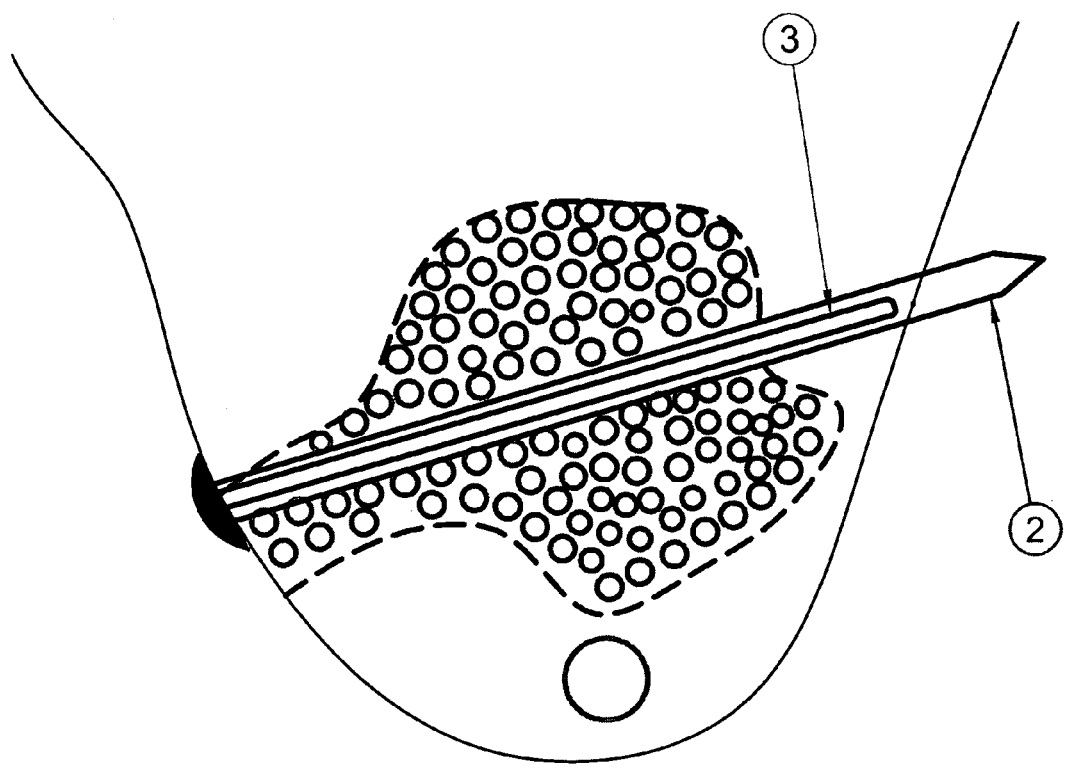
FIG. 5 illustrates the brachytherapy guide tube inside of the hollow trocar.
Figure 6:
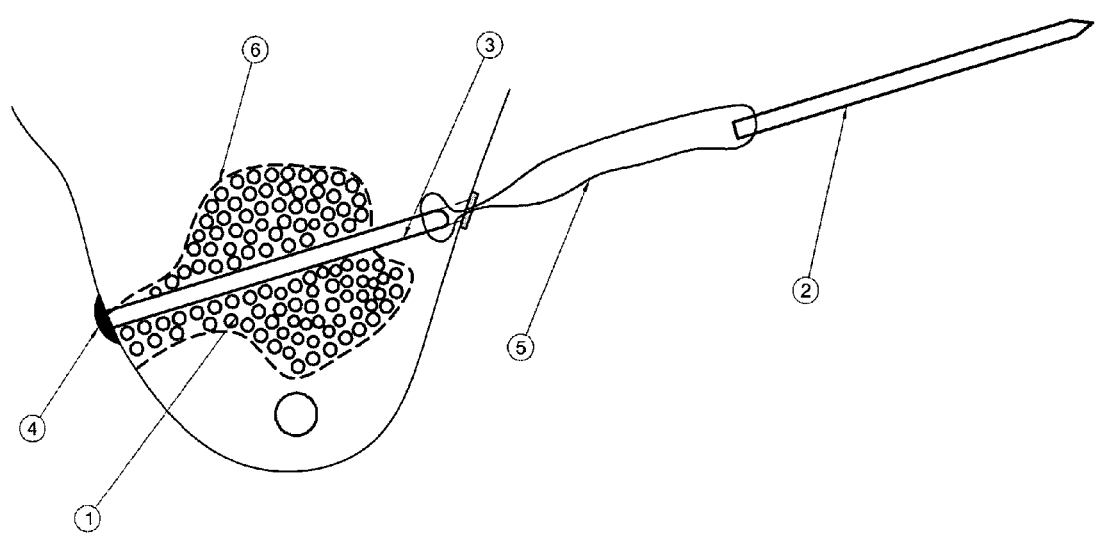
FIG. 6 illustrates the trocar in the removed position and the brachytherapy guide tube ready for suturing to the skin

The brachytherapy guide tube (3) is inserted into the hollow trocar (2) and positioned so that the distal end of the brachytherapy guide tube is just under the skin on the far side of the breast, where the trocar exits the breast (FIG. 5). The trocar (2) is pulled through the breast while the surgeon holds and stabilizes the brachytherapy guide tube so that it does not move. The sutures (5) are exposed on the far side of the breast (FIG. 6). The surgeon severs the sutures from the trocar and sutures the distal end of the brachytherapy guide tube to the skin so that the distal end for the brachytherapy guide tube is under the skin.

Figure 7:
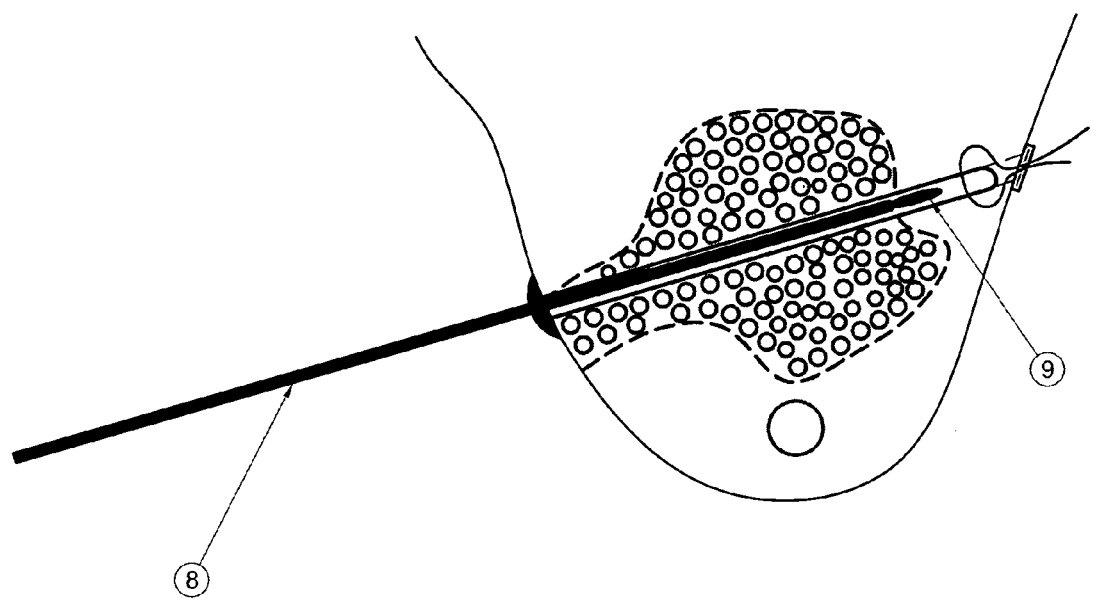
FIG. 7 illustrates the brachytherapy catheter positioned inside of the brachytherapy guide tube.
Figure 8:
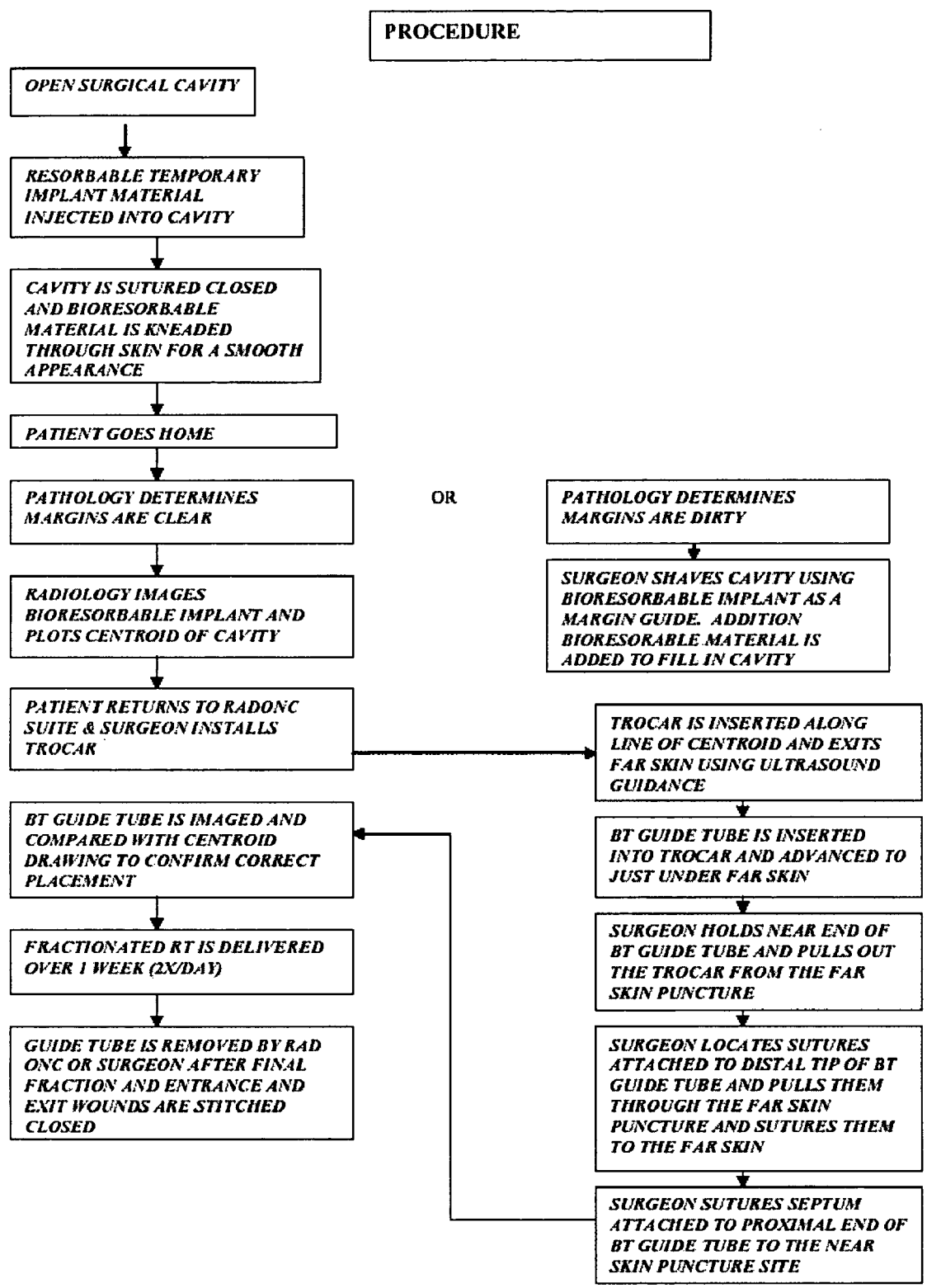
FIG. 8 describes procedural steps in delivering limited field radiation to the breast with the breast brachytherapy applicator, in an open surgical cavity procedure.
Figure 9:
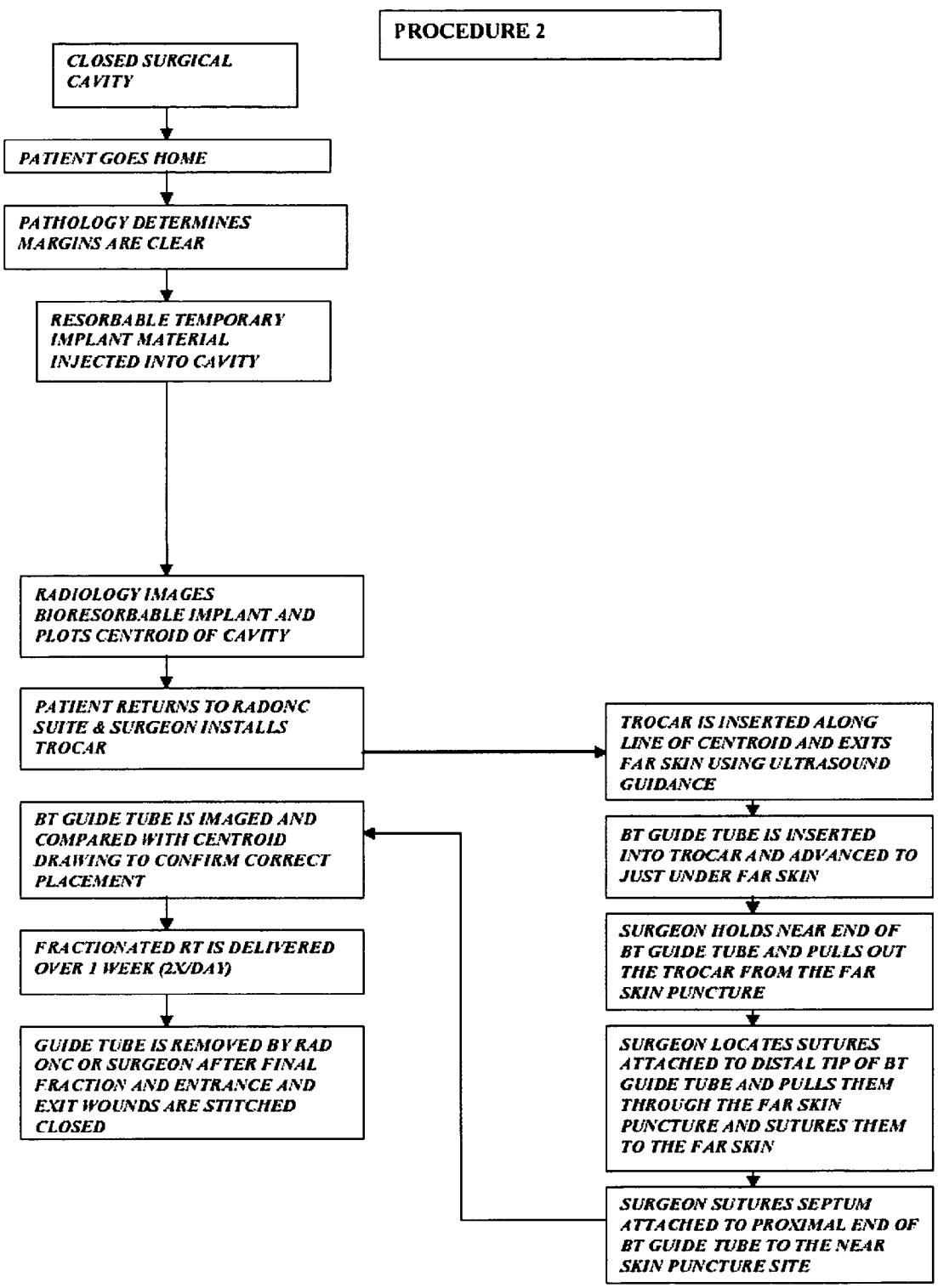
FIG. 9 describes procedural steps in delivering limited field radiation to the breast with the breast brachytherapy applicator, in a closed surgical cavity procedure.

The surgeon then sutures the elastomeric septum (4) to the near side breast skin. The elastomeric septum (4) provides a sealed port for introducing a brachytherapy catheter or probe. The elastomeric septum (4) preferably comprises silicone, pebax, polyurethane or any of a variety of other suitable elastomeric, biocompatible materials. The elastomeric septum provides a sealed, infection resistant system between radiation fractions, providing the patient with an unobtrusive device that does not protrude from the breast. The elastomeric septum can be coated or embedded with silver or platinum particles to help resist infection. FIG. 7 shows a brachytherapy catheter (8) positioned inside of the brachytherapy guide tube.

The bulking media or tissue scaffold may comprise any of a number of materials known in the art. PEG hydrogels are suitable materials that can be tailored so that they biodegrade over different lengths of time, depending on the application. Nektar Therapeutics, San Carlos, Calif. is one manufacturer of these materials. Other good candidates for implant material include porous gelatins, collagen, polyanhydrides, polyglycolic acid, polylactic/polyglycolic copolymers, polyhydroxybutyrate-valerate and other aliphatic polymers.

Suitable soft gels may additionally include injectable, cross-linked hyaluronic acids such as Hylaform from Genzyme or from Inamed (Santa Barbara, Calif.). Alternatively, a bioresorbable thermal reversal gel may be utilized. Such gels are liquid at room temperature, but form a gel at body temperature. One suitable gel may be Regel, available from MacroMed. Hard gels may be provided in a variety of ways, which are understood in the art. In general, such gels transform into the hardened state based upon the change in solubility as the polymer is transferred from a biocompatible solvent into the aqueous environment of a water containing cavity.

Preferably, the bulking material will degrade over time to allow replacement by native tissue and other native byproducts of the healing process. This is facilitated if the bulking media is selected such that breakdown products which may be released as the bulking media degrades do not unduly interfere with the healing process. Polylactic (PLA) and polyglycolic (PGA) based polymer and copolymers are known to generate glycolic acid and lactic acid in their final phase of degradation. Depending upon the geometry of the implant and the size of the implant, the amount of acid may have negative effects on the body, which may influence specific design and concentration criteria. Other bulking media such as hydrogels may be selected which do not include PLA/PGA, or may contain only a relatively smaller amount of PLA and/or PGA in their formulation. This allows a reduction in the amount of acid compared to an implant made entirely of PLA and/or PGA or their derivatives.

In general, the rate of degradation of the tissue scaffold may be selected depending upon the desired clinical performance. For example, tissue ingrowth may occur more quickly in smaller cavities. For this reason, a bulking media with a more rapid degradation rate may be desirable in relatively smaller cavities, while a longer degradation, may be desirable in a larger tissue cavity. For a spherical cavity having a diameter of about 3 cm the media may desirably degrade in about 6 to 12 months. The present inventors contemplate a degradation period of about 3 to 9 months for smaller cavities. However, other degradation rates may be utilized depending upon the desired performance of the tissue scaffold in a particular patient.

When used with biodegradable bulking media, the present invention thus provides a declining volume tissue support which provides continuous support for the excisional cavity throughout a range of cavity volumes. At the same time, the bulking media may transform in its three dimensional configuration to facilitate growth of adjacent tissue, regardless of the geometry of the tissue cavity.

The tissue support scaffold may additionally serve as a drug delivery vehicle. Chemotherapeutic drugs and antibiotics among other therapeutic substances can be incorporated into the scaffold.

Any of a variety of known technologies may be utilized, for incorporating a drug into or on to the bulking media, for delivery over a period of time. The selection of a particular technology will depend upon the desired drug, the desired bulking media, and the desired drug delivery time period as will be appreciated by those of skill in the art in view of the disclosure herein.

Although the present invention has been described in terms of certain preferred embodiments, other embodiments can be readily devised by one of skill in the art in view of the foregoing, which will also use the basic concepts of the present invention. Accordingly, the scope of the present invention is not intended to be limited by the foregoing discussion, but should rather be defined by reference to the attached claims.

What is claimed is:

1. A method of performing brachytherapy on a patient following breast cancer surgery, comprising the steps of:
    performing a therapeutic surgical lumpectomy or wide surgical excision of a breast to remove a malignant tumor, leaving a surgical cavity surrounded by a margin of native tissue;
    introducing a stabilizing medium comprising collagen into the cavity to anatomically fix the position of the margin; and
    delivering a radiation dose from within the cavity to at least the margin using a radiation source placed into the stabilizing medium.

2. A method of performing brachytherapy following breast cancer surgery, comprising the steps of:
    performing a therapeutic surgical lumpectomy or wide surgical excision of a breast to remove a malignant tumor, leaving a surgical cavity surrounded by a margin of native tissue;
    introducing a stabilizing medium into the cavity to anatomically fix the position of the margin;
    positioning a guide tube through the medium by advancing a hollow trocar through the medium, advancing the guide tube through the trocar, and removing the trocar to leave the guide tube in place through the bulking medium; and placing a radiation source into the guide tube so that the source is within the stabilizing medium, and delivering a radiation dose using the radiation source, to at least the margin.

3. A method of performing brachytherapy following breast cancer surgery, comprising the steps of:
performing a therapeutic surgical lumpectomy or wide surgical excision of a breast to remove a malignant tumor, leaving a surgical cavity surrounded by a margin of native tissue;
introducing a stabilizing medium into the cavity to anatomically fix the position of the margin;
positioning a guide through the medium, and securing a proximal end of the guide to a dermal surface, and
placing a radiation source into the stabilizing medium while guiding the source using the guide, and delivering a radiation dose from within the cavity to at least the margin.

4. A method of performing brachytherapy following breast cancer surgery, comprising the steps of:
performing a therapeutic surgical lumpectomy or wide surgical excision of a breast to remove a malignant tumor, leaving a surgical cavity surrounded by a margin of native tissue;
introducing a stabilizing medium into the cavity to anatomically fix the position of the margin;
positioning a guide through the medium, and securing a distal end of the guide to a dermal surface, and
placing a radiation source into the stabilizing medium while guiding the source using the guide, and delivering a radiation dose from within the cavity to at least the margin.

5. A method of positioning a brachytherapy guide through a surgically excised cavity, comprising the steps of:
creating a cavity by therapeutic surgical resection or wide surgical excision, excising a volume of tissue, the cavity defined within a margin of remaining tissue;
introducing a bulking medium into the cavity to stabilize the original anatomical position of the margin;
imaging the location of the margin;
determining at least one axis of desired radiation therapy taking into account the position of the margin; and
introducing a brachytherapy guide along the axis and into the bulking medium.

6. A method of positioning a brachytherapy guide as in claim 5, wherein the imaging step is accomplished post-operatively to geometrically determine the configuration of the tissue surrounding the surgical cavity.

7. A method of positioning a brachytherapy guide as in claim 5, wherein the introducing a brachytherapy guide step comprises introducing a trocar along the axis, and advancing the guide along the path of the trocar.

8. A method of positioning a brachytherapy guide as in claim 6, further comprising the step of removing the trocar, leaving the guide in place along the axis.

* * * * *